United States Patent
Fujita et al.

Patent Number: 5,219,884
Date of Patent: Jun. 15, 1993

[54] IMMUNOSUPPRESSANT

[75] Inventors: Tetsuro Fujita, Muko; Takeshi Ikumoto; Shigeo Sasaki, both of Kobe; Takeki Okumoto; Kenji Chiba, both of Tokyo, all of Japan

[73] Assignees: Taito Co., Ltd., Tokyo; Yoshitomi Pharmaceutical Industries, Ltd., Osaka, both of Japan

[21] Appl. No.: 465,201

[22] PCT Filed: Sep. 14, 1988

[86] PCT No.: PCT/JP88/00933
§ 371 Date: Mar. 1, 1990
§ 102(e) Date: Mar. 1, 1990

[87] PCT Pub. No.: WO90/02727
PCT Pub. Date: Mar. 22, 1990

[51] Int. Cl.$^5$ .................... A61K 31/34; C07D 307/32
[52] U.S. Cl. .................... 514/472; 514/558; 514/560; 549/313; 549/318; 554/108; 554/110
[58] Field of Search .......... 549/475, 318, 313; 514/472, 560, 558; 260/404; 554/108, 110

[56] References Cited

U.S. PATENT DOCUMENTS

| | | | |
|---|---|---|---|
| 3,758,529 | 9/1973 | Craveri et al. | 260/404 |
| 4,375,475 | 3/1983 | Willard et al. | 549/292 |
| 4,857,546 | 8/1989 | Duggen et al. | 49/292 |

Primary Examiner—C. Warren Ivy
Assistant Examiner—A. A. Owens
Attorney, Agent, or Firm—Wenderoth, Lind & Ponack

[57] ABSTRACT

The present invention relates to an immunosuppressive agent which comprises at least one compound selected from the compounds of formula

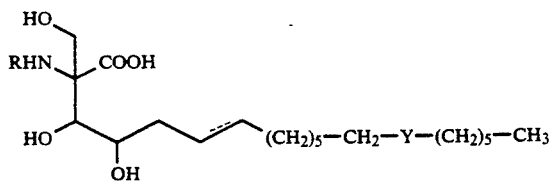

wherein R represents a hydrogen atom or an acyl, Y represents carbonyl or hydroxymethylene and ⚌ represents a single bond or a double bond and their lactones, in an effective amount and a pharmaceutically acceptable carrier; a method of prophylaxis and therapy for suppressing rejection or autoimmune diseases which comprises administering the above-mentioned compound or its lactone in an effective amount; and a novel compound of formula

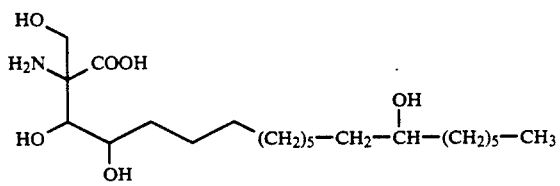

or its lactone.

3 Claims, No Drawings

IMMUNOSUPPRESSANT

TECHNICAL FIELD

This invention relates to the new uses of the extracts from a certain kind of microorganisms including genus Isaria and their analogues, and their related novel compounds.

BACKGROUND ART AND DISCLOSURE OF THE INVENTION

As an immunosuppressant known heretofore, ciclosporin can be mentioned. Ciclosporin has been used for suppression of rejection in transplantation of the kidney and possesses an excellent immunosuppressive effect.

Ciclosporin, however, has a drawback that it causes side effects (e.g. renal disturbances, hepatic disturbances).

Therefore, there has been demanded immunosuppressants which have potent immunosuppressive activities and the lowest possible side effects.

From such a viewpoint, the present inventors have conducted extensive studies to find that the compounds of the formula (I) mentioned below which include novel compound and their lactone possessed excellent immunosuppressive activities while having lower side effects, and further studies have led to the completion of the present invention.

That is, this invention relates to immunosuppressive agents which comprise at least one compound selected from the compounds of formula

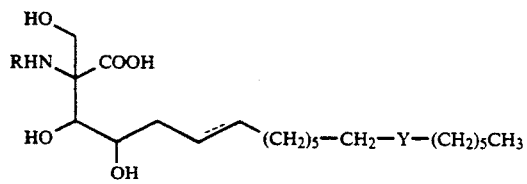

(I)

wherein R represents a hydrogen atom or an acyl, Y represents carbonyl or hydroxymethylene and ▭ bond represents a single bond or a double bond [hereinafter referred to as compounds (I)] and their lactones, in an effective amount and a pharmaceutically acceptable carrier, to a method for suppressing rejection or a method of prophylaxis and therapy for autoimmune diseases which comprises administering at least one compound selected from compounds (I) and their lactones in an effective amount, and to a compound of the formula (I-1)

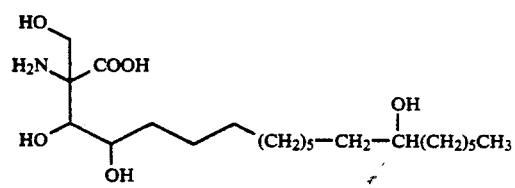

(I-1)

and its lactone.

Referring to R in the present specification, mention is made of, for example, alkanoyls having 2 to 5 carbon atoms such as acetyl, propionyl, butyryl, pivaloyl, etc. and aromatic acyls having 7 to 11 carbon atoms such as benzoyl, phenylacetyl, etc as the acyl.

Preferred compounds (I) and their lactones are as shown below:

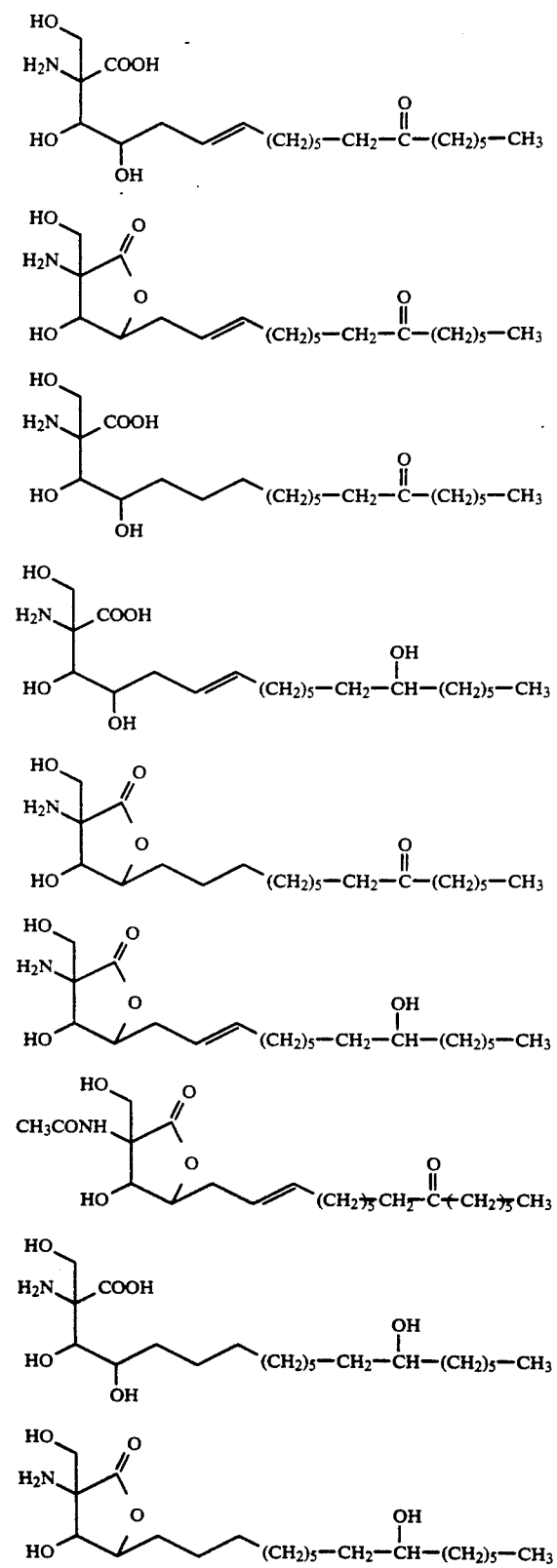

Among the above-mentioned compounds, the last two compounds, namely, the compound of the formula (I-1) and its lactone are novel compounds.

The compound of the formula (I) wherein R is a hydrogen atom, is a double bond and Y is carbonyl which is the compound obtained in accordance with Example 1 mentioned hereafter, namely, ISP-I is known as Myriocin or Thermozymocidin [See The Journal of Antibiotics, vol. XXV No. 2, 109-115 (1972), The Journal of Organic Chemistry, 38(7), 1253-1260 (1973), J. Chem. Soc. Perkin Trans. I, 1613-1619 (1983), J. Chem. Soc., Chem. Commun., 488-490 (1982) etc.], with its action being an antifungal action.

Compounds (I) and their lactones can be produced by fermentation method or synthesis method in accordance with, for example, the following Production Methods 1-5.

The production method for ISP-I has been disclosed in the above literatures as well.

Production Method 1 (Fermentation Method)

ISP-I can be usually produced by fermenting an ISP-I-producing microorganism and collecting ISP-I from the culture. As the microorganisms to be used, mention is made of, for example, those belonging to Ascomycotina and Deuteromycotina, more specifically, genus Isaria and genus Mycelia belonging to Deuteromycotina and genus Myriococcus (Thielavia) belonging to Ascomycotina, which are respectively deposited at American Type Culture Collection as *Isaria sinclairii* ATCC No. 74121, *Myriococcum albomyces* ATCC No. 74120 and *Mycelia sterilia* ATCC No. 74122, under terms of the Budapest Treaty.

ISP-I can also be produced by a mutant which can be obtained by modification of a strain mentioned above by way of a conventional artificial mutating means such as ultraviolet rays, microwave radioactive rays and chemicals.

ISP-I producing microorganisms can be cultivated in various culture-media comprising usual nutrient sources for fungi. For example, there can be suitably added glucose, starches, glycerine, sugar millet jelly, dextrin, molasses, maltose, xylose, and the like as carbon sources; inorganic or organic nitrogen compounds such as corn steep liquor, peptone, yeast extract, potato extract, meat extract, soy bean meal, wheat germ, potassium nitrate, sodium nitrate, ammonium sulfate, casein, gluten meal, cotton seed meal, feather meal as nitrogen sources; other conventional inorganic salts; and conventional additives for cultivation, such as organic and inorganic substances and antifoaming agents which help growth of microorganisms and can promote the production of ISP-I.

Though there is no particular limitation to the cultivation method thereof, aerobic submerged cultivation is more advantageous. The preferable culture temperature in the case of strains belonging to genus Isaria is in the range from 20° C. to 35° C., more preferably 25° C. to 30° C., and that in the case of strains of genus Myriococcum or Mycelia is in the range from 30° C. to 50° C., preferably 35° C. to 45° C.

The ISP-I produced in the culture can be harvested from the culture by conventional procedures such as extraction, adsorption or by combination of conventional procedures. For example, in the case of strains such as *Isaria sinclairii* belonging to genus Isaria, insoluble matters such as cells are removed by a separation method such as filtration or centrifugation, and the resulting culture filtrate is put in contact with Amberlite XAD-2 to adsorb the ISP-I for harvesting. The thus-obtained ISP-I is dissolved in methanol, and the dissolved objective ISP-I is subjected to reverse phase chromatography for fractionation to obtain highly purified ISP-I. In the case of strains such as *Myriococcum albomyces* and *Mycelia sterilia* which belong to genus Myriococcum or genus Mycelia, cells are removed from the culture by a separation method such as filtration and centrifugation, and the culture filtrate is subjected to the same procedure as that in the case of strains of genus Isaria. Meanwhile, ISP-I is extracted from the separated cells with methanol and the extract is subjected to Amberlite XAD-2 as for the filtrate, followed by further purification such as chromatography or recrystallization to give ISP-I.

The compounds (I) and their lactones other than ISP-I can be produced, for example, by the following methods.

Production Method 2 (Synthesis Method)

The lactones of the compounds (I) can be produced by ① treating the corresponding compounds (I) including ISP-I with an inorganic acid such as hydrochloric acid or an organic acid such as acetic acid or ② treating them with a tertiary alcohol such as tert-amyl alcohol.

The reaction ① can be conducted usually in the presence of a solvent inert to the reaction (e.g. an alcohol such as methanol or ethanol). The reaction temperature is usually in the range from 0° C. to 50° C., preferably about room temperature, and the reaction time is usually 10 to 30 hours, preferably about 20 hours.

The reaction temperature in the reaction ② is usually in the range from 80° C. to 150° C., preferably 100° C. to 120° C. The reaction time is usually 10 to 30 hours, preferably about 20 hours.

Production Method 3 (Synthesis Method)

Among the compounds (I) including ISP-I, the compounds (I) wherein ⎓ is a single bond and their lactones can be produced by hydrogenating the corresponding compounds (I) wherein ⎓ is a double bond and their lactones.

Such hydrogenation is conducted in the presence of a conventional catalyst such as a palladium compound, a nickel compound or a platinum compound. The reaction is usually conducted in the presence of a solvent (e.g. an alcohol such as methanol or ethanol). The reaction temperature usually ranges from 0° C. to 50° C., preferably about room temperature, and the reaction time is usually 1 to 10 hours, preferably about several hours.

Production Method 4 (Synthesis Method)

The compounds (I) wherein Y is hydroxymethylene and their lactones can be produced by reducing the corresponding compounds (I) wherein Y is carbonyl or their lactones.

The reduction reaction can be conducted by a metal hydrogen complex compound such as sodium borohydride or lithium aluminum hydride.

The reaction is conducted usually in the presence of a solvent (e.g. an alcohol such as methanol or ethanol). The reaction temperature is usually 0°-50° C., preferably about room temperature, and the reaction time is usually 0.5-4 hours, preferably about 1 hour.

Production Method 5 (Synthesis Method)

The compounds (I) wherein R is an acyl or their lactones can be produced by acylating the corresponding compounds (I) wherein R is a hydrogen atom or their lactones by a per se known means.

As the acylating agent to be used for the acylation, mention is made of, for example, acid anhydrides, acid halides, active esters and the like.

The acylation reaction can be carried out under per se known conditions.

The compounds (I) and their lactones possess excellent immunosuppressive actions, and therefore are usable as a suppressive agent for rejection in organ or marrow transplantation, as a prophylactic or therapeutic agent for autoimmune diseases such as rheumatoid arthritis, systemic lupus erythematosus, Sjogren's syndrome, multiple sclerosis, grave myasthenia, I-type diabetes, endocrine ophthalmopathy, primary biliary cirrhosis, Crohn's diseases, glomerulonephritis, sarcoidosis, psoriasis, pemphigus, hypoplastic anemia, idiopathic thrombocytopenic purpura and allergy, or as a medical and pharmaceutical reagent to humans, cattles, horses, dogs, mice, rats and so on.

The compounds (I) or their lactones are admixed with carriers, excipients, diluents and the like to be formulated into dosage forms such as powders, capsules, tablets, injections for administration to patients. They may also be lyophilized into a pharmaceutical composition by a per se known means.

While the dosage of the compounds (I) or their lactones varies depending on diseases, symptoms, body weight, sex, age and so on, for the suppression in kidney transplantation, for example, they can be usually administered at the daily dosage per adult of 0.1–10 mg (potency), in one to several divided doses.

EXAMPLES

The following examples will illustrate this invention in more detail, though this invention should not be restricted to these examples as far as it comes within the scope of this invention. Immunosuppressive activities were assayed by the following methods.

Said activities are assayed based on various immune reactions using mouse, rat and human lymphocytes; for example, immunosuppressive activities are assayed with high sensitivity by using mouse, rat or human allogenic mixed lymphocyte reactions (allogenic MLR). Allogenic MLR is blastogenesis of lymphocytes induced by mixed culture of lymphocytes derived from two individuals that are allogenic but different in their major histocompatibility antigens, such as spleen cells, lymphnode cells and peripheral blood lymphocytes. This allogenic MLR is a reaction representing a phenomenon which reflects the difference in the major histocompatibility antigens among the donors; for example, blastogenesis of lymphocytes cannot be observed by the mixed culture of lymphocytes from monozygotic twins. Therefore, allogenic MLR is widely used for selection of the donor and the recipient in organ transplantation.

It is usual for allogenic MLR that the lymphocytes from one of the two donors are used as stimulator cells after treatment with X-ray irradiation or with mitomycin C to inhibit their mitotic proliferation, while blastogenesis of the lymphocytes from the other donor (responder cells) is measured (one way-MLR).

Immunosuppressive activities can be determined also by measuring the activities to suppress the induction of major histocompatibility antigens-restricted cytotoxic T cells in allogenic MLR.

In addition, immunosuppressive activities can be evaluated also as the activities to suppress blastogenesis of lymphocytes induced by stimulation with various mitogens (e.g. concanavalin A, phytohemagglutinin, pokeweed mitogen, etc.), or as the activities to suppress the mitotic proliferation or induction of functions of lymphocytes induced by cytokines (e.g. interleukin 1, 2, 3, 4, 5, 6, etc.) which enhance the mitotic proliferation or promote differentiation of lymphocytes such as T cells and B cells. Immunosuppressive activities can also be evaluated as the activities to suppress the production of such cytokines from T cells, macrophages, etc.

Immunosuppressive activities can also be evaluated as the activities to suppress the induction of plasma cells producing the anti-xenogenic red blood cell antibodies induced within mouse spleen cells which have been immunized in advance with xenogenic red blood cells, etc. by intraperitoneal, oral, intravenous or intradermal injection to mice, or as the activities to suppress rejection in organ transplantation from allogenic mice, graft-versus-host reaction, delayed allergy, adjuvant arthritis, etc.

Furthermore, immunosuppressive activities can be evaluated as the suppression of production of anti-DNA antibody, production of rheumatoid factor, nephritis, abnormal proliferation of lymphocytes, or as the life-prolonging effect in MRL/lpr mice, NZB/WF$_1$ mice or BXSB mice, which are the model mice of autoimmune diseases, by the administration of the compounds (I) or their lactones.

EXAMPLE 1

(i) Jar cultivation of *Isaria sinclairii*

One hundred ml of the GPY medium (30 g of glucose, 5 g of peptone, 3 g of yeast extract, 0.3 g of KH$_2$PO$_4$, 0.3 g of K$_2$HPO$_4$ and 0.3 g of MgSO$_4$·7H$_2$O in one liter, pH 5.5) was placed into each of two 500 ml-long-neck shaking flasks, and autoclaved at 121° C. for 20 minutes, followed by inoculation of about 1 cm$^2$ of mycelia of *Isaria sinclairii* ATCC No.74121 grown on the potato dextrose agar medium, which was then incubated at 25° C. for 6 days in a reciprocal shaker (145 rpm, amplitude: 8 cm). The resultant culture was inoculated as the seed into the 10 l-fermentation jar in which 5 l of the GPY medium described above had been placed, which was then subjected to aerobic spinner culture (1 VVM, 300 rpm) at 25° C. for 10 days.

(ii) Collection of ISP-I from the culture of *Isaria sinclairii*

From 4.5 l of the culture obtained in (i) cells and insoluble matters were removed by filtration to give 4.0 l of culture filtrate. The obtained culture filtrate was allowed to pass through a column of Amberlite XAD-2 ($\phi$ mm×750 mm) so that ISP-I could be adsorbed. The column was washed with 4.0 l of water. Then 6 l of methanol was allowed to pass to elute ISP-I. The eluate was concentrated under reduced pressure, dissolved in 200 ml of ethyl acetate, and extracted 3 times each with 200 ml of water in a separatory funnel.

The extract with water and that with ethyl acetate were separately concentrated under reduced pressure, and freeze-dried to give 2.23 g and 0.34 g, respectively, of ISP-I.

(iii) Purification of ISP-I

ISP-I (2.23 g) obtained in (ii) by freeze-drying of the water extract was dissolved in 5 ml of water and fed to the column for reverse phase chromatography (ODS DM-1020T manufactured by Fuji-Devison Chemicals, Co.) (φ mm×h85 mm). Elution was begun with water, and fractionation was carried out by gradient elution with increasing methanol concentration. The fractions eluted with 70% methanol were concentrated to dryness under reduced pressure, dissolved in a small amount of hot methanol, and allowed to cool to give crystals of ISP-I. The crystals were dissolved again in hot methanol for recrystallization to give 40 mg of pure ISP-I.

EXAMPLE 2 (i) Jar cultivation of *Myriococcum albomyces*

One hundred ml of the GCY medium (20 g of glucose, 5 g of corn steep liquor, 3 g of yeast extract and 0.5 g of $MgSO_4 \cdot 7H_2O$ in one liter, pH 6) was placed into each of two 500 ml-long-neck shaking flasks, and autoclaved at 121° C. for 20 minutes, followed by inoculation of about 1 $cm^2$ of mycelia of Myriococcum albomyces ATCC No. 74120 grown on the potato dextrose agar medium, which was then incubated at 40° C. for 3 days in a reciprocal shaker (145 rpm, amplitude: 8 cm). The resultant culture was inoculated as the seed into the 10 l -fermentation jar in which the GCY medium described above and 1 g of an antifoaming agent (F-18 manufactured by Dow Coning Co.) had been placed, which was then subjected to aerobic spinner culture (0.5 VVM, 300 rpm) at 40° C. for 7 days.

(ii) Collection of ISP-I from the culture of *Myriococcum albomyces*

From 4.5 l of the culture obtained in (i) cells were removed and the culture filtrate was obtained. The culture filtrate (4 l) was allowed to pass through a column of Amberlite XAD-2 (φ 40mm×h750 mm) so that ISP-I could be adsorbed. The column was washed with 1 l of water. Then 1 l of 30% methanol, 1 l of 50% methanol and 3 l of 80% methanol were allowed to pass in this order, and the eluate with 80% methanol containing ISP-I was collected.

Separately, the cells were extracted 3 times with methanol of an amount about 5 times that of the wet weight of the cells, and water was added to the extract to give a 30% methanol solution, which was then allowed to flow through a column of Amberlite XAD-2 (φ40 mm×h750 mm) so that ISP-I could be adsorbed. One liter of 30% methanol, 1 l of 50% methanol and 3 l of 80% methanol were allowed to flow in this order, and the eluate with 80% methanol containing ISP-I was collected.

The fractions eluted with 80% methanol from the culture filtrate and from the cells obtained as described above were combined, concentrated under reduced pressure, and freeze-dried to give 0.5 g of powders containing ISP-I.

(iii) Purification of ISP-I

The powders (0.5 g) containing ISP-I obtained in (ii) was washed with ethyl acetate and then with hot water (60° C.), dissolved in hot methanol, and allowed to cool to give crystals of ISP-I. Repeated recrystallization from methanol gave 250 mg of ISP-I.

EXAMPLE 3

(i) Jar cultivation of *Mycelia sterilia*

*Mycelia sterilia* ATCC No. 74122 was cultivated in the same manner as in Example 2 (i).

(ii) Collection of ISP-I from the culture of *Mycelia sterilia*

In the same way as in Example 2 (ii), 1 g of powders containing ISP-I was obtained.

(iii) Purification of ISP-I

In the same way as in Example 2 (iii), 600 mg of ISP-I was obtained.

The physical properties of the ISP-I obtained in Examples 1 to 3 are as follows.

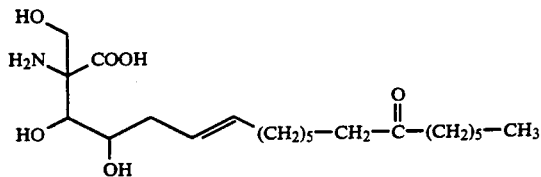

melting point: 172°–177° C.
$^1$H-NMR δ(ppm $CD_3OD$) : 5.52(m), 5.39(m), 3.99(d), 3.87(d), 3.83(m), 3.78(d)
IR ν(KBr) : 3400, 1710, 1670, 1605, 970 $cm^{-1}$

EXAMPLE 4

One hundred mg of ISP-I was dissolved in 20 ml of methanol, to which 0.4 ml of 44% methanolic hydrochloric acid was added, and kept standing overnight at room temperature, and thereafter the solvent was evaporated off under reduced pressure. The residue was purified by chromatography on silica gel (10 g) using a mixture of chroloform and methanol (9:1), followed by recrystallization from chloroform-petroleum ether to give 75 mg of the compound having the following structure formula.

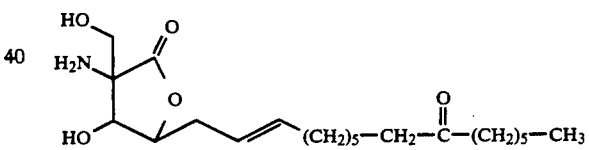

The physical properties of the compound thus obtained are as follows:
melting point: 75°–76° C.
$^1$H-NMR δ(ppm $CDCl_3$) : 5.62(m), 5.43(m), 4.48(m), 4.14(d), 3.75(d), 3.66(d)
IR ν($CHCl_3$) 3400, 1770, 1705, 975 $cm^{-1}$

EXAMPLE 5

Fifty mg of ISP-I was dissolved in 15 ml of methanol and the solution was subjected to hydrogenation using 5% palladium carbon (40 mg) as the catalyst. Palladium carbon was filtrated off, the solvent was evaporated under reduced pressure, and repeated recrystallization from methanol gave 38 mg of the compound having the following structural formula.

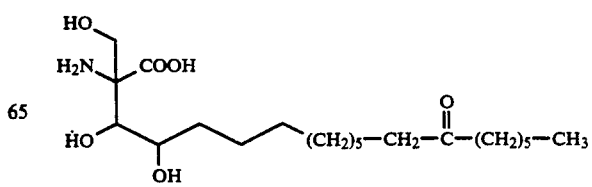

The physical properties of the compound are as follows:
melting point: 154°-155.5° C.
$^1$H-NMR δ(ppm CD$_3$OD) : 3.99(d), 3.87(d), 3.81(m), 3.87(d)
IR ν(KBr) : 3400, 1715, 1670 cm$^{-1}$

EXAMPLE 6

Fifty mg of ISP-I was dissolved in 15 ml of methanol, to which sodium borohydride (20 mg) was added little by little. Thirty minutes later, 1 ml of a saturated ammonium chloride solution was added to stop the reaction, followed by extraction with chloroform and recrystallization from methanol to give 46 mg of the compound having the following structural formula.

[Structure: HO, H$_2$N, COOH, HO, OH, (CH$_2$)$_5$—CH$_2$—CH—(CH$_2$)$_5$—CH$_3$, OH]

The physical properties of the compound thus obtained are as follows:
melting point: 162°-165° C.
$^1$H-NMR δ(ppm CD$_3$OD) : 5.52(m), 5.38(m), 3.99(d) 3.87(d), 3.82(m), 3.78(s), 3.48(m)
IR ν(KBr) : 3300, 1665, 1635, 970 cm$^{-1}$

EXAMPLE 7

The compound obtained in Example 5 was treated in the same way as in Example 4 and the compound having the following structural formula was obtained.

[Structure: HO, H$_2$N, O, O, HO, (CH$_2$)$_5$—CH$_2$—C—(CH$_2$)$_5$—CH$_3$, O]

The physical properties of the compound are as follows:
melting point: 96°-98° C.
$^1$H-NMR δ(ppm CDCl$_3$) 4.49(t), 4.13(s), 3.72(m)
IR ν(KBr) : 3400, 1770, 1720 cm$^{-1}$

EXAMPLE 8

The compound obtained in Example 6 was treated in the same way as in Example 4 and the compound having the following structural formula was obtained.

[Structure: HO, H$_2$N, O, O, HO, (CH$_2$)$_5$—CH$_2$—CH—(CH$_2$)$_5$—CH$_3$, OH]

The physical properties of the compound are as follows:
melting point: 55°-56° C.
$^1$H-NMR δ(ppm CDCl$_3$) 5.61(m), 5.44(m), 4.48(m), 4.14(d), 3.72(d), 3.66(d), 3.57(m)
IR νKBr) : 3350, 1760, 975 cm$^{-1}$

EXAMPLE 9

The compound obtained in Example 5 was treated in the same way as in Example 6 and the compound having the following structural formula was obtained.

[Structure: HO, H$_2$N, COOH, HO, OH, (CH$_2$)$_5$—CH$_2$—CH—(CH$_2$)$_5$—CH$_3$, OH]

The physical properties of the compound are as follows: melting point: 161°-162° C.
$^1$H-NMR δ(ppm CD$_3$OD) : 4.00(d), 3.88(d), 3.81(m), 3.74(s), 3.49(m)
IR νKBr) : 3300, 1630 cm$^{-1}$

EXAMPLE 10

The compound obtained in Example 9 was treated in the same way as in Example 4 and the compound having the following structural formula was obtained.

[Structure: HO, H$_2$N, O, O, HO, (CH$_2$)$_5$—CH$_2$—CH—(CH$_2$)$_5$—CH$_3$, OH]

The physical properties of the compound are as follows:
melting point: 71.5°-72.5° C.
$^1$H-NMR δ(ppm CDCl$_3$) 4.49(m), 4.11(d), 3.74(d), 3.69(d), 3.58(m)
IR νKBr) : 3350, 1760 cm$^{-1}$

EXAMPLE 11

One hundred mg of ISP-I was dissolved in 30 ml of methanol, to which 10 ml of acetic anhydride was added, kept standing overnight at room temperature. Water was added to decompose acetic anhydride, and the solvent was evaporated off under reduced pressure. The residue was purified by chromatography on silica gel (10 g) using chloroform-methanol (9:1) to give 60 mg of the compound having the following structural formula.

[Structure: HO, CH$_3$CONH, O, O, HO, (CH$_2$)$_5$CH$_2$—C—(CH$_2$)$_5$CH$_3$, O]

The physical properties of the compound are as follows: melting point: 105.5°-107° C.
$^1$H-NMR δ(ppm CDCl$_3$) : 6.59(s), 5.62(m), 5.42(m), 4.66(m), 4.60(m)
IR νKBr) : 3300, 1760, 1710, 1650, 975 cm$^{-1}$

EXPERIMENTAL EXAMPLE

Experimental Example 1 (Immunosuppressive activity of immunosuppressive compounds)

The immunosuppressive activity of the compounds (I) and their lactones was assayed by using mouse allogenic mixed lymphocyte reaction (hereinafter sometimes abbreviated as MLR). Mouse allogenic MLR was carried out by mixed culture of the BALB/c mouse (H-2$^d$) spleen cells as the responder cells and the mitomycin C-treated C57BL/6 (H-2$^b$) spleen cells as the stimulator cells in equal amounts.

The responder cells were prepared as follows: The spleen was resected from 5- to 6-week-old male BALB/c mice, and single cell suspension of spleen cells was prepared by using the RPMI1640 culture medium (containing 60 μg/ml of kanamycin sulfate, 2 mM of L-glutamine, 10 mM of N-2-hydroxyethylpiperazine-N'-2-ethanesulfonate (HEPES) and 0.1% sodium hydrogencarbonate) to which heat-inactivated fetal calf serum (hereinafter sometimes abbreviated as FCS) had been added to 5%. After hemolytic treatment, the cell suspension was adjusted to a concentration of $10^7$ cells/ml by using the RPMI1640 culture medium supplemented with $10^{-4}$ M 2-mercaptoethanol and 20% FCS, and was used as the responder cell suspension.

The stimulator cells were prepared as follows:

The spleen was resected from 5- to 6-week-old male C57BL/6 mice, and single cell suspension of spleen cells was prepared by using the RPMI1640 culture medium. After hemolytic treatment, the cells were treated with 40 μg/ml of mitomycin C at 37° C. for 60 minutes. After washing three times, the concentration of the cell suspension was adjusted to $10^7$ cells/ ml by using the RPMI1640 culture medium supplemented with $10^{-4}$ M 2-mercaptoethanol and 20% FCS, and was used as the stimulator cell suspension.

Fifty μl of the responder cell suspension, 50μl of the stimulator cell suspension prepared by the above method, and 100 μl of the test substance were placed in 96-well microculture plates, and were cultured at 37° C. in an atmosphere of 5% carbon dioxide for 4 days.

The blastogenesis of lymphocytes was assayed by a method of $^3$H-thymidine uptake as an index. That is, after termination of the culture, 0.5 μCi/well of $^3$H-thymidine was added and cultured for 4 hours. Cells were harvested by a cell-harvester, and the radioactivity incorporated into the cells was determined by a liquid scintillation counter to obtain the index of blastogenesis of lymphocytes in the mouse allogenic MLR. The suppression of the mouse allogenic MLR was evaluated by calculating the percent suppression by the following formula. The results are summarized in Tables 1A to 1D.

$$\text{percent suppression} (\%) = \left[1 - \frac{\text{cpm in MLR with test substance} - \text{cpm with responder cells alone}}{\text{cpm in MLR without test substance} - \text{cpm in responder cells alone}}\right] \times 100$$

TABLE 1A

| Responder cell | Stimulator cell | Test substance | Dose (μg/ml) | $^3$H-thymidine uptake (cpm) | Suppression (%) |
|---|---|---|---|---|---|
| BALB/c | — | — | — | 963 | — |
| — | C57BL/6 | — | — | 124 | — |
| BALB/c | C57BL/6 | — | — | 14375 | — |
| BALB/c | C57BL/6 | compound of Example 1 | 0.001 | 14760 | 0 |
| | | compound of Example 1 | 0.01 | 6436 | 59.2 |
| | | compound of Example 1 | 0.1 | 686 | 100.0 |
| | | compound of Example 1 | 1 | 698 | 100.0 |

TABLE 1B

| Responder cell | Stimulator cell | Test substance | Dose (μg/ml) | $^3$H-thymidine uptake (cpm) | Suppression (%) |
|---|---|---|---|---|---|
| BALB/c | — | — | — | 2125 | — |
| — | C57BL/6 | — | — | 491 | — |
| BALB/c | C57BL/6 | — | — | 29716 | — |
| BALB/c | C57BL/6 | compound of Example 4 | 0.001 | 29598 | 0.4 |
| | | compound of Example 4 | 0.01 | 10394 | 70.0 |
| | | compound of Example 4 | 0.1 | 1414 | 100.0 |

TABLE 1C

| Responder cell | Stimulator cell | Test substance | Dose (μg/ml) | $^3$H-thymidine uptake (cpm) | Suppression (%) |
|---|---|---|---|---|---|
| BALB/c | — | — | — | 6195 | — |
| — | C57BL/6 | — | — | 55 | — |
| BALB/c | C57BL/6 | — | — | 27267 | — |
| BALB/c | C57BL/6 | compound of Example 5 | 0.001 | 22321 | 23.5 |
| | | compound of Example 5 | 0.01 | 8182 | 90.6 |
| | | compound of Example 5 | 0.1 | 1952 | 100.0 |
| | | compound of Example 6 | 0.001 | 16237 | 52.3 |
| | | compound of Example 6 | 0.01 | 9276 | 85.4 |
| | | compound of Example 6 | 0.1 | 3017 | 100.0 |
| | | compound of Example 7 | 0.001 | 24446 | 13.4 |
| | | compound of Example 7 | 0.01 | 34378 | 0 |
| | | compound of Example 7 | 0.1 | 3546 | 100.0 |
| | | compound of Example 8 | 0.001 | 22815 | 21.1 |
| | | compound of Example 8 | 0.01 | 3081 | 100.0 |
| | | compound of Example 8 | 0.1 | 1586 | 100.0 |
| | | compound of Example 9 | 0.001 | 25682 | 7.5 |
| | | compound of Example 9 | 0.01 | 23668 | 17.1 |
| | | compound of Example 9 | 0.1 | 3167 | 100.0 |
| | | compound of Example 10 | 0.001 | 19595 | 36.4 |
| | | compound of Example 10 | 0.01 | 19019 | 39.1 |
| | | compound of Example 10 | 0.1 | 2405 | 100.0 |
| | | compound of Example 11 | 0.001 | 32597 | 0 |
| | | compound of Example 11 | 0.01 | 30777 | 0 |
| | | compound of Example 11 | 0.1 | 23430 | 18.2 |

The test substance was dissolved in methanol or suspended in a mixture of methanol and acetic acid, and then diluted with the RPMI1640 culture medium. Methanol and acetic acid were used at a concentration of less than 0.01%, and they did not affect the allogenic MLR at all.

The compounds (1) and their lactones in the final concentration range of 1 μg/ml to 0.001 μg/ml were examined for their suppressive activity for blastogenic response of lymphocytes in mouse allogenic MLR. As shown in Tables 1A to D, ISP-I was suppressive in mouse allogenic MLR, with the 50%-inhibition concentration ($IC_{50}$) being $7.1 \times 10^{-3}$ μg/ml. The activities of other compounds (I) and their lactones were comparable to that of ISP-I, with the $IC_{50}$ values being about 1/10 that of cyclosporin A or less. However, these compounds even at the concentration of 10 μg/ml were not cytotoxic to mouse L929 cells ($IC_{50}$ was 10 μg/ml or more).

Blastogenesis of lymphocytes can be evaluated also by the following colorimetry using 3-(4,5-dimethyl-thiazol-2-yl)2,5-diphenyltetrazolium bromide (MTT).

Ⓒ Colorimetry using MTT

The supernatant (100 μl) is removed from each well after termination of the culture, and 20 μl of the 5 mg/ml MTT solution is added to each well, which is cultured at 37° C. for 4 hours. Thereafter, 100 μl of a 0.01 N hydrochloric acid solution containing 10% sodium dodecylsulfate is added thereto and cultured at 37° C. overnight to dissolve the resultant purple crystals of formazan. The absorbancy at 550 nm is measured using a microplate absorption spectrophotometer as an index of blastogenic response of lymphocytes in mouse allogenic MLR. Suppression of mouse allogenic MLR is evaluated by calculating the percent suppression by the following formula:

$$\text{percent suppression (\%)} = \left(1 - \frac{\text{absorbancy in MLR with test substance} - \text{absorbancy in responder cells alone}}{\text{absorbancy in MLR without test substance} - \text{absorbancy in responder cells alone}}\right) \times 100$$

Experimental Example 2 (Human allogenic MLR-suppressive activity)

The human allogenic MLR-suppressive activity was assayed as follows:

Human peripheral blood lymphocytes obtained by Ficoll-Paque density gradient centrifugation of normal human peripheral blood were suspended in the RPMI1640 medium supplemented with 10% FCS, placed in plastic dishes, and incubated at 37° C. in an atmosphere of 5% carbon dioxide for 2 hours. After termination of incubation, the supernatant after gentle pipetting was harvested and centrifuged (1000 rpm, for 5 minutes) to obtain plastic-nonadherent cells. The plastic-nonadherent cells were allowed to pass through a nylon-wool column to give nylon-nonadherent cells, and the concentration of the cell suspension was adjusted to $4 \times 10^6$ cells/ml by using the RPMI1640 culture medium supplemented with 10% FCS, and used as the responder cell suspension.

The plastic-adherent cells were removed from the plastic dish by vigorous pipetting after addition of phosphate buffered saline supplemented with 5% FCS and 0.02% disodium ethylenediamine-tetraacetic acid (EDTA). The plastic-adherent cells were treated with 40 μg/ml of mitomycin C at 37° C. for 60 minutes, washed three times, and suspended to the concentration of $4 \times 10^6$ cells/ml in the RPMI1640 culture medium supplemented with 10% FCS. The resultant suspension was used as the stimulator cell suspension. Fifty μl of the responder cell suspension from the donor A or C was mixed with 50 μl of the stimulator cell suspension from the donor B or D, to which 100 μl of the test substance was added, and cultured at 37° C. in the an atmosphere 5% carbon dioxide for 5 days.

After termination of the culture, 1.0 μCi/well of $^3$H-thymidine was added, and after 18 hours of culture, the cells were harvested by a cell-harvester. The radioactivity incorporated into the cells was measured by a liquid scintillation counter as the index of blastogenic response of lymphocytes in human allogenic MLR. The suppression of human allogenic MLR was evaluated by calculating the percent suppression by the following formula:

$$\text{percent suppression (\%)} = \left(1 - \frac{\text{cpm in MLR with test substance} - \text{cpm with responder cells alone}}{\text{cpm in MLR without test substance} - \text{cpm in responder cells alone}}\right) \times 100$$

The compounds (1) and their lactones in the final concentration range of 10 μg/ml to $10^{-5}$ μg/ml were examined for their suppressive activity for blastogenic response of lymphocytes in human allogenic MLR. As shown in Tables 2A and 2B, the 50%-inhibition concentration ($IC_{50}$) of ISP-I in Example 1 of this invention in the human allogenic MLR was $1.0 \times 10^{-4}$ μg/ml, $IC_{50}$ of the compound in Example 4 was $7.9 \times 10^{-4}$ μg/ml, $IC_{50}$ of the compound in Example 6 was $2.2 \times 10^{-4}$ μg/ml, and IC 50 of the compound in Example 5 was $3.5 \times 10^{-4}$ μg/ml.

Based on the results shown in Tables 2A and 2B, the $IC_{50}$ values of the compounds (I) and their lactones in human allogenic MLR were found to be lower than that of ciclosporin A.

TABLE 2A

| Responder cell | Stimulator cell | Test substance | Dose (μg/ml) | $^3$H-thymidine uptake (cpm) | Suppression (%) |
|---|---|---|---|---|---|
| Donor A | — | — | — | 2408 | — |
| — | Donor B | — | — | 118 | — |
| Donor A | Donor B | — | — | 23891 | — |
| Donor A | Donor B | compound of Example 1 | 0.0001 | 12769 | 51.8 |
| | | compound of Example 1 | 0.001 | 7190 | 77.7 |
| | | compound of Example 1 | 0.01 | 8138 | 73.3 |
| | | compound of Example 1 | 0.1 | 6922 | 79.0 |
| | | compound of Example 1 | 1 | 6690 | 80.1 |
| | | compound of Example 1 | 10 | 1082 | 100.0 |
| | | compound of Example 4 | 0.0001 | 16963 | 32.3 |
| | | compound of Example 4 | 0.001 | 13715 | 47.4 |
| | | compound of Example 4 | 0.01 | 9754 | 65.8 |
| | | compound of Example 4 | 0.1 | 4734 | 89.2 |
| | | compound of Example 4 | 1 | 5954 | 83.5 |
| | | compound of Example 4 | 10 | 5332 | 86.4 |
| | | compound of Example 5 | 0.0001 | 20789 | 14.4 |
| | | compound of Example 5 | 0.001 | 14690 | 42.8 |
| | | compound of Example 5 | 0.01 | 11130 | 59.4 |
| | | compound of Example 5 | 0.1 | 5181 | 87.1 |

TABLE 2A-continued

| Responder cell | Stimulator cell | Test substance | Dose (μg/ml) | ³H-thymidine uptake (cpm) | Suppression (%) |
|---|---|---|---|---|---|
| | | compound of Example 5 | 1 | 5548 | 85.4 |
| | | compound of Example 5 | 10 | 2439 | 99.8 |
| | | compound of Example 6 | 0.0001 | 14191 | 45.2 |
| | | compound of Example 6 | 0.001 | 11753 | 56.2 |
| | | compound of Example 6 | 0.01 | 6335 | 81.7 |
| | | compound of Example 6 | 0.1 | 6418 | 81.3 |
| | | compound of Example 6 | 1 | 5877 | 83.9 |
| | | compound of Example 6 | 10 | 4564 | 90.0 |

TABLE 2B

| Responder cell | Stimulator cell | Test substance | Dose (μg/ml) | ³H-thymidine uptake (cpm) | Suppression (%) |
|---|---|---|---|---|---|
| Donor C | — | — | — | 89 | — |
| — | Donor D | — | — | 56 | — |
| Donor C | Donor D | — | — | 17427 | — |
| Donor C | Donor D | compound of Example 1 | 0.00001 | 10896 | 37.7 |
| | | compound of Example 1 | 0.0001 | 9806 | 44.0 |
| | | compound of Example 1 | 0.001 | 5646 | 67.9 |
| | | compound of Example 1 | 0.01 | 4460 | 74.8 |
| | | compound of Example 1 | 0.1 | 3613 | 79.2 |
| | | compound of Example 1 | 1 | 4167 | 76.5 |
| | | compound of Example 1 | 10 | 2018 | 88.8 |
| | | compound of Example 4 | 0.00001 | 7746 | 55.8 |
| | | compound of Example 4 | 0.0001 | 6700 | 61.9 |
| | | compound of Example 4 | 0.001 | 7278 | 58.5 |
| | | compound of Example 4 | 0.01 | 3417 | 80.8 |
| | | compound of Example 4 | 0.1 | 2708 | 84.9 |
| | | compound of Example 4 | 1 | 3703 | 79.2 |
| | | compound of Example 4 | 10 | | |
| | | compound of Example 5 | 0.00001 | 11827 | 32.3 |
| | | compound of Example 5 | 0.0001 | 7941 | 54.7 |
| | | compound of Example 5 | 0.001 | 9057 | 48.3 |
| | | compound of Example 5 | 0.01 | 7346 | 58.1 |
| | | compound of Example 5 | 0.1 | 2746 | 84.7 |
| | | compound of Example 5 | 1 | 3466 | 80.5 |
| | | compound of Example 5 | 10 | | |
| | | compound of Example 6 | 0.00001 | 16241 | 6.8 |
| | | compound of Example 6 | 0.0001 | 14996 | 14.0 |
| | | compound of Example 6 | 0.001 | 8468 | 51.7 |
| | | compound of Example 6 | 0.01 | 4082 | 77.0 |
| | | compound of Example 6 | 0.1 | 3501 | 80.3 |
| | | compound of Example 6 | 1 | 2448 | 86.4 |

Experimental Example 3 [Suppression of induction of alloreactive cytotoxic T cells in mouse allogenic mixed lymphocyte culture (MLC)]

The spleen cells suspension, 0.5 ml, (2×10⁷ cells/ml) of BALB/c mouse (H-2$^d$) prepared in the same way as in Experimental Example 1, 0.5 ml of a suspension of mitomycin C-treated C57BL/6 mouse (H-2$^b$) spleen cells (2×10⁷ cell/ml) and 1.0 ml of the test substance were added to 24-well multidishes, and cultured at 37° C. in an atmosphere of 5% carbon dioxide for 6 days.

After termination of the culture, the cells were harvested by centrifugation, and the concentration of the cell suspension was adjusted to 5×10⁶–6.25×10⁵ cells/ml by using the RPMI1640 culture medium supplemented with 10% FCS, and used as the effector cell suspension.

The target cells used were leukemia cells EL4 from the syngenic (H-2$^b$) C57BL/b mouse as used for preparation of the stimulator cells. By incubating 10⁶ EL4 cells in the presence of 100 μCi of Na₂⁵¹CrO₄ (1 mCi/ml) at 37° C. for 1 hour to incorporate ⁵¹Cr into the cytoplasm. The cell were washed, adjusted to the concentration of 10⁴ cells/ml and used as the target cell suspension.

For the assay of the cytotoxic activity, 0.1 ml of the effector cell suspension and 0.1 ml of the target cell suspension were added to 96-well flat-bottomed plates, and cultured at 37° C. for 4 hours. The amount of ⁵¹Cr released into the supernatant was determined and the cytotoxic activity was calculated by the following formula.

$$\text{cytotoxic activity (\%)} = \left(1 - \frac{\frac{\text{cpm, effector cells + target cells}}{\text{cpm, total radioactivity}} - \frac{\text{cpm, target cells alone}}{\text{cpm, target cells alone}}}{}\right) \times 100$$

The cytotoxic T cells induced by the method described above exhibited strong cytotoxic activity to the EL4 cells (H-2$^b$) which are syngenic with the stimulator cells (H-2$^b$) whereas they were not cytotoxic to the allogenic Meth A cells (H-2$^d$), and thus it was suggested that they were H-2$^b$-restricted allo-reactive cytotoxic T cells.

As shown in Table 3, addition of the compound (I) or a lactone thereof markedly inhibited the induction of the allo-reactive cytotoxic T cells and at the same time cytotoxic activity was hardly observed.

TABLE 3

| Test substance | Dose (μg/ml) | Amount of ⁵¹Cr release (cpm) | Cytotoxic activity (%) |
|---|---|---|---|
| Total radioactivity of target cells | — | — | 2179 | — |

TABLE 3-continued

| | Test substance | Dose (μg/ml) | Amount of $^{51}$Cr release (cpm) | Cytotoxic activity (%) |
|---|---|---|---|---|
| Target cells alone | — | — | 788 | 0 |
| Effector cells + target cells (100:1) | — | — | 1392 | 43.4 |
| (50:1) | — | — | 983 | 14.0 |
| (25:1) | — | — | 996 | 15.0 |
| Effector cells + target cells (100:1) | compound of Example 1 | 0.01 | 808 | 1.4 |
| (50:1) | | 0.01 | 783 | 0 |
| (25:1) | | 0.01 | 816 | 2.0 |
| Effector cells + target cells (100:1) | compound of Example 1 | 0.1 | 771 | 0 |
| (50:1) | | 0.1 | 773 | 0 |
| (25:1) | | 0.1 | 764 | 0 |
| Effector cells + target cells (100:1) | compound of Example 4 | 0.1 | 761 | 0 |
| (50:1) | | 0.1 | 780 | 0 |
| (25:1) | | 0.1 | 767 | 0 |

Experimental Example 4 (Suppression of blastogenic response of mouse spleen cells by mitogen stimulation)

The effect on the mouse blastogenic response of mouse spleen cells stimulated with phytohemagglutinin (PHA) or with pokeweed mitogen (PWM) was examined as follows:

The spleen was resected from 5- to 8-week-old male spleen cells BALB/c mice, and single cell suspension of spleen cells was prepared by using the RPMI1640 culture medium supplemented with 5% FCS. After hemolytic treatment, the concentration of the suspension was adjusted to $5 \times 10^6$ cells/ml by using the RPMI1640 culture medium supplemented with $10^{-4}$ M 2-mercaptoethanol and 20% FCS, to which PHA or PWM was added. One hundred μl of the cell suspension was added to each well of 96-well microculture plates to which 100 μl per well of the test solution had been added ($5 \times 10^5$ mouse spleen cells per well). After culturing at 37° C. in an atmosphere of 5% carbon dioxide for 72 hours, 0.5 μCi/well of $^3$H-thymidine was added and cultured under the same conditions for further 4 hours. After termination of the culture, the cells were harvested by a cell harvester, and the radioactivity incorporated into the cells was measured by a liquid scintillation counter, which was used as the index of blastogenic response of mouse spleen cells. The results are summarized in Table 4.

TABLE 4

| Mitogen | Test substance | Dose (μg/ml) | $^3$H-thymidine uptake (cpm) | Suppression (%) |
|---|---|---|---|---|
| — | — | — | 1109 | — |
| PHA(1/100) | — | — | 8693 | — |
| PHA(1/100) + | compound of Example 1 | 0.01 | 3238 | 71.9 |
| | | 0.1 | 3624 | 66.8 |
| | | 1 | 1686 | 92.4 |
| PHA(1/100) + | compound of Example 4 | 0.01 | 6074 | 34.5 |
| | | 0.1 | 4312 | 57.8 |
| | | 1 | 3308 | 71.0 |
| — | — | — | 1916 | — |
| PWM(1/100) | — | — | 31646 | — |
| PWM(1/100) + | compound of Example 1 | 0.01 | 13499 | 61.0 |
| | | 0.1 | 9895 | 73.2 |
| | | 1 | 6529 | 84.5 |
| PWM(1/100) + | compound of Example 4 | 0.01 | 19335 | 41.4 |
| | | 0.1 | 9325 | 75.1 |
| | | 1 | 8712 | 77.1 |

As shown in Table 4, the compounds (I) and their lactones strongly inhibited the incorporation of $^3$H-thymidine induced by PHA or PWM as compared with the control without the compounds.

Experimental Example 5 (Suppression of the interleukin 1 (IL1) response of mouse thymocytes)

The thymus was resected from 7-week-old male C3H/HeN mice, and single cell suspension was prepared using the serum-free RPMI1640 culture medium. After three times washing with the medium, the cells were suspended to a concentration of $1.5 \times 10^7$ cells/ml in the RPMI1640 culture medium supplemented with 20% fetal calf serum, $5 \times 10^{-5}$ M 2-mercaptoethanol, $2 \times 10^{-3}$ M L-glutamine, $1 \times 10^{-3}$ M sodium pyruvate, 1 μg/ml of phytohemagglutinin (PHA, Wellcome Co., HA16/17) and 2 units/ml of human ultrapure interleukin 1 (Genzyme Co., GUPi-1). One hundred μl of this cell suspension and 100 μl of the solution containing ISP-I were mixed in each well of the 96-well flat-bottomed microculture plate, cultured at 37° C. in an atmosphere of 5% carbon dioxide for 66 hours, and cultured for further 6 hours after addition of 0.5 μCi/well of $^3$H-thymidine. After termination of the culture, the cells in each well were harvested onto a filter by a multiple cell harvester, and the radioactivity incorporated into the cells was measured by liquid scintillation method using a toluene-base scintillator.

The results obtained are summarized in Table 5. In the table, SD means standard deviation. The percent suppression (%) was calculated by the following formulation.

$$\text{percent suppression (\%)} = \left\{ 1 - \frac{\begin{pmatrix} {}^3\text{H-thymidine incorporated with PHA} + \\ \text{IL1} + \text{test substance} \end{pmatrix} - \begin{pmatrix} {}^3\text{H-thymidine incorporated with PHA alone} \end{pmatrix}}{\begin{pmatrix} {}^3\text{H-thymidine incorporated with PHA} + \text{IL1} \end{pmatrix} - \begin{pmatrix} {}^3\text{H-thymidine incorporated with PHA alone} \end{pmatrix}} \right\} \times 100$$

TABLE 5

| Test substance | Dose (μg/ml) | $^3$H-thymidine uptake (cpm ± SD) | Suppression (%) |
|---|---|---|---|
| — | — | 1389 ± 42 | — |
| PHA | — | 3270 ± 316 | — |
| PHA + IL1 + compound of Example 1 | — | 11803 ± 1740 | 0 |
| | 2 | 3973 ± 39 | 91.8 |
| | 0.2 | 4646 ± 826 | 83.9 |

As shown in Table 5, it is evident that the compound (I) and the lactones thereof show suppression of the IL1 response in a dose-dependent manner.

Experimental Example 6 (Suppression of IL2 production in mouse allogenic mixed lymphocyte culture (MLC) and in PHA-stimulated mouse spleen cells)

Mouse allogenic MLC was carried out as follows:

The respondor cell suspension and the stimulator cell suspension (0.5 ml each) prepared in the same way as in Experimental Example 1 together with 1 ml of test substance were added to 24-well multidishes, and cultured at 37° C. in an atmosphere of 5% carbon dioxide for 2 days. After termination of the culture, the supernatant was collected and used as the supernatant of mouse allogenic MLC.

Culture of PHA-stimulated mouse spleen cells was carried out as follows: PHA (1/100 dilution) was added to the BALB/c mouse spleen cells suspension prepared in the same way as in Experimental Example 4. The cell suspension (1 ml) and 1 ml of the test substance were added to 24-well multidishes, and cultured at 37° C. in an atmosphere of 5% carbon dioxide for 24 hours. After termination of the culture, the supernatant was collected and used as the supernatant of PHA-stimulated cultures.

The IL2 activity in the supernatants of mouse allogenic MLC and the supernatants of PHA-stimulated mouse spleen cells culture was assayed as follows: IL2-dependent mouse cell line CTLL-2 cells were suspended in the RPMI1640 culture medium supplemented with 30% FCS to the concentration of $10^5$ cells/ml, and 100 μl of the suspension was added to each well of 96-well microculture plates in which 100 μl of the supernatant of the MLC described above had been placed. After culturing at 37° C. in an atmosphere of 5% carbon dioxide for 20 hours, 0.5 μCi/well of $^3$H-thymidine was added, and incubated for 4 hours under the same conditions. After termination of the culture, the cells were harvested by a cell harvester, and the radioactivity incorporated into the cells was measured by a liquid scintillation counter. IL2 activity was expressed in U/ml as the titer at various concentrations at which the $^3$H-thymidine incorporation was 50% of the maximum. The results are summarized in Table 6.

TABLE 6

| Sample | IL2 activity (U/ml) | Suppression (%) |
|---|---|---|
| culture supernatant of responder cells alone | <1 | — |
| Culture supernatant of Untreated MLC | 9.8 | — |
| Supernatant of MLC treated with compound of Example 1 | | |
| (0.01 μg/ml) | 4.0 | 59.2 |
| (0.1 μg/ml) | 2.0 | 79.6 |
| (1 μg/ml) | 1.1 | 88.8 |
| (10 μg/ml) | <1 | >90 |
| Supernatant of MLC treated with compound of Example 4 | | |
| (0.01 μg/ml) | 4.0 | 59.2 |
| (0.1 μg/ml) | 1.7 | 82.7 |
| (1 μg/ml) | <1 | >90 |
| (10 μg/ml) | <1 | >90 |
| Unstimulated culture supernatant | <1 | — |
| Culture supernatant stimulated with PHA | 12.1 | — |
| PHA-stimulated culture supernatant treated with compound of Example 1 | | |
| (0.01 μg/ml) | 6.5 | 46.3 |
| (0.1 μg/ml) | 2.5 | 79.3 |
| (1 μg/ml) | 1.1 | 90.9 |
| (10 μg/ml) | <1 | >92 |
| PHA-stimulated culture supernatant treated with compound of Example 4 | | |
| (0.01 μg/ml) | 4.9 | 59.5 |
| (0.1 μg/ml) | 2.6 | 78.5 |
| (1 μg/ml) | <1 | >92 |
| (10 μg/ml) | <1 | >92 |

As shown in Table 6, it was suggested that the compounds (I) and their lactones suppress the production of IL2 in mouse allogenic MLC and in the PHA-stimulated mouse spleen cells.

Experimental Example 7 [Suppression of IL-2 induced $^3$H-thymidine incorporation of IL2-dependent mouse cell line CTLL-2]

IL2-dependent mouse cell line CTLL-2 cells were suspended in the RPMI1640 culture medium supplemented with 30% FCS to a concentration of $2 \times 10^5$ cells/ml. The suspension (50 μl) and 50 μl of concanavalin A-stimulated rat spleen cell culture supernatants containing IL2 were added to each well of 96-well microculture plates in which 100 μl of the test substance had been placed. After culturing at 37° C. in an atmosphere of 5% carbon dioxide for 20, 44, or 68 hours, 0.5 μCi/well of $^3$H-thymidine was added, and cultured for 4 hours under the same conditions. After termination of the culture, the cells were harvested by a cell harvester, and the radioactivity incorporated into the cells was measured by a liquid scintillation counter. The results are summarized in Table 7.

TABLE 7

| Incubation time | IL2 | Test substance | Dose (μg/ml) | $^3$H-thymidine uptake (cpm) | Suppression (%) |
|---|---|---|---|---|---|
| 24 hrs. | — | — | — | 185 | — |
| | + | — | — | 6671 | — |
| | + | compound of Example 1 | 0.01 | 6003 | 10.3 |
| | + | | 0.1 | 3722 | 45.5 |
| | + | | 1 | 3977 | 41.5 |
| | + | | 10 | 1968 | 72.5 |
| | + | compound of Example 4 | 0.01 | 5907 | 11.8 |
| | + | | 0.1 | 4240 | 37.5 |
| | + | | 1 | 5400 | 19.6 |
| | + | | 10 | 2602 | 62.7 |
| 48 hrs. | — | — | — | 436 | — |
| | + | — | — | 25216 | — |
| | + | compound of Example 1 | 0.01 | 19592 | 22.7 |
| | + | | 0.1 | 7324 | 72.2 |
| | + | | 1 | 4794 | 82.4 |
| | + | | 10 | 1649 | 95.1 |
| | + | compound of Example 4 | 0.01 | 21930 | 13.3 |
| | + | | 0.1 | 9202 | 64.6 |
| | + | | 1 | 7202 | 72.7 |
| | + | | 10 | 7465 | 71.6 |
| 72 hrs. | — | — | — | 683 | — |
| | + | — | — | 78515 | — |
| | + | compound of Example 1 | 0.01 | 56688 | 28.0 |
| | + | | 0.1 | 2436 | 97.7 |
| | + | | 1 | 846 | 99.8 |

TABLE 7-continued

| Incubation time | IL2 | Test substance | Dose (μg/ml) | 3H-thymidine uptake (cpm) | Suppression (%) |
|---|---|---|---|---|---|
| | + | | 10 | 478 | 100.0 |
| | + | compound of Example 4 | 0.01 | 69355 | 11.8 |
| | + | | 0.1 | 16705 | 79.4 |
| | + | | 1 | 4088 | 95.6 |
| | + | | 10 | 11806 | 85.7 |
| 72 hrs. | — | — | — | 56 | — |
| | + | — | — | 30168 | — |
| | + | compound of Example 5 | 0.1 | 26108 | 13.5 |
| | + | | 1 | 1532 | 95.1 |
| | + | compound of Example 6 | 0.1 | 7237 | 76.2 |
| | + | | 1 | 1346 | 95.7 |
| | + | compound of Example 7 | 0.1 | 37960 | 0 |
| | + | | 1 | 2088 | 93.3 |
| | + | compound of Example 8 | 0.1 | 7262 | 76.1 |
| | + | | 1 | 1591 | 94.9 |
| | + | compound of Example 9 | 0.1 | 33835 | 0 |
| | + | | 1 | 2247 | 92.7 |
| | + | compound of Example 10 | 0.1 | 28083 | 6.9 |
| | + | | 1 | 1844 | 94.1 |
| | + | compound of Example 11 | 0.1 | 33948 | 0 |
| | + | | 1 | 4876 | 84.0 |

As shown in Table 7, the compounds (I) and their lactones strongly suppressed IL2-induced 3H-thymidine incorporation of CTLL-2 cells.

Experimental Example 8 (Suppression of induction of interleukin 2 receptor (IL-2R, Tac) expression in mouse allogenic MLC and PHA-stimulated mouse spleen cells)

Mouse allogenic MLC and PHA-stimulated mouse spleen cells were prepared in the same as in Experimental Example 3.

The IL-2R (Tac) induced in mouse allogenic MLC and PHA-stimulated mouse spleen cells was assayed as follows:

After culturing the mouse allogenic MLC and the PHA-stimulated mouse spleen cells at 37° C. in an atmosphere of 5% carbon dioxide for 24 hours, the cells were collected by centrifugation (1000 rpm, 5 minutes, 4° C.), and about $10^6$ cells were cultured in 10 μl of phosphate buffered saline (PBS), to which 0.02% sodium azide-containing rat anti-mouse IL-2R monoclonal antibody (manufactured by Boehringer Co., 40 μg/ml) had been added, for 30 minutes with ice-cooling. After washing three times with ice-cooled PBS containing 0.02% sodium azide, 50 μl of fluorescein isothiocyanate (FITC)-labeled goat anti-rat immunoglobulin G antibody was added and cultured for 30 minutes with ice-cooling. To the cell pellet after washing three times with ice-cooled 0.02% sodium azide-added PBS was added, a few drops of PBS containing 0.2% sodium azide and 50% glycerin. Prepared specimens on non-fluorescent slide glasses were made and the IL-2R positive cells were counted under a fluorescent microscope to determine the ratio of numbers of IL-2R positive cells in the total numbers of the cells.

TABLE 8

| | IL-2R positive cells (%) | Suppression (%) |
|---|---|---|
| Respondor cells | 0 | — |
| Untreated MLC cells | 24.4 | — |
| MLC cells treated with compound of Example 1 | | |
| (0.001 μg/ml) | 22.4 | 8.2 |
| (0.01 μg/ml) | 17.6 | 27.9 |
| (0.1 μg/ml) | 13.1 | 44.3 |
| (1 μg/ml) | 11.4 | 53.3 |
| Unstimulated spleen cells | 0 | — |
| Untreated PHA-stimulated spleen cells | 46.2 | — |
| PHA-stimulated spleen cells treated with compound of Example 1 | | |
| (0.1 μg/ml) | 36.6 | 20.8 |
| (1 μg/ml) | 26.6 | 42.4 |
| (10 μg/ml) | 13.4 | 71.0 |

As shown in Table 8, it was suggested that the compounds (I) and their lactones suppress the expression of IL-2R induced by stimulation with the alloantigen and with PHA in a concentration-dependent manner.

Experimental Example 9 (Suppression of IL3 production in mouse allogenic MLC and PHA-stimulated mouse spleen cells)

The supernatant of mouse allogenic MLC and the supernatant of PHA-stimulated mouse spleen cells culture were prepared in the same manner as in Experimental Example 6.

The IL3 activity in the supernatant described above was assayed as follows: IL3-dependent mouse cell line FDC-P2 cells were suspended in the RPMI1640 culture medium supplemented with 10% FCS to the concentration of $10^5$ cells/ml, and 100 μl of the suspension was added to each well of 96-well microculture plates in which 100 μl per well of the two-fold serial dilutions of the supernatant described above had been placed. After culturing at 37° C. in an atmosphere of 5% carbon dioxide for 20 hours, 0.5 μCi/well of 3H-thymidine was added, and cultured for further 4 hours under the same conditions. After termination of the culture, the cells were harvested by a cell harvester, and the radioactivity incorporated into the cells was measured by a liquid scintillation counter. The IL3 activity was expressed in U/ml as the titer at the concentrations at which the amount of 3H-thymidine incorporated was 50% of the maximum. The results are summarized in Table 9.

TABLE 9

| Sample | IL3 activity (U/ml) | Suppression (%) |
|---|---|---|
| culture supernatant of responder cells alone | <2 | — |
| Culture supernatant of Untreated MLC | 36.8 | — |
| Supernatant of MLC treated with compound of Example 1 | | |
| (0.01 μg/ml) | 13.9 | 62.2 |
| (0.1 μg/ml) | 12.1 | 67.1 |
| (1 μg/ml) | 9.8 | 73.4 |
| (10 μg/ml) | <2 | >95 |
| Supernatant of MLC treated with compound of Example 4 | | |
| (0.01 μg/ml) | 26.0 | 29.3 |
| (0.1 μg/ml) | 16.0 | 56.5 |
| (1 μg/ml) | 8.6 | 76.6 |

TABLE 9-continued

| Sample | IL3 activity (U/ml) | Suppression (%) |
|---|---|---|
| (10 μg/ml) | 6.1 | 83.4 |
| Unstimulated culture supernatant | <2 | — |
| Culture supernatant stimulated with PHA | 17.1 | — |
| PHA-stimulated culture supernatant treated with compound of Example 1 | | |
| (0.01 μg/ml) | 4.0 | 76.6 |
| (0.1 μg/ml) | <2 | >90 |
| (1 μg/ml) | <2 | >90 |
| (10 μg/ml) | <2 | >90 |
| PHA-stimulated culture supernatant treated with compound of Example 4 | | |
| (0.01 μg/ml) | 9.1 | 46.8 |
| (0.1 μg/ml) | 2.8 | 83.6 |
| (1 μg/ml) | 2.3 | 86.5 |
| (10 μg/ml) | <2 | >90 |

As shown in Table 9, it was suggested that the compounds (I) and their lactones suppress the IL3 production in mouse allogenic MLC and PHA-stimulated mouse spleen cells.

Experimental Example 10 [Suppression of proliferation of IL3-dependent mouse cell line FDC-P2 induced by interluekin 3 (IL3)]

IL3-dependent mouse cell line FDC-P2 cells were suspended in the RPMI1640 culture medium supplemented with 10% FCS to the concentration of $2 \times 10^5$ cells/ml. One hundred μl of the suspension and 50 μl of the supernatant of the culture of mouse luekemia cells WEHI3 containing IL3 were added to each well of 96-well microculture plates in which 100 μl of the test substance had been placed. After culturing at 37° C. in an atmosphere of 5% carbon dioxide for 20 hours, 0.5 μCi/well of $^3$H-thymidine was added, and cultured for 4 hours under the same conditions. After termination of the culture, the cells were harvested by a cell harvester, and the radioactivity incorporated into the cells was determined by a liquid scintillation counter, and was used as an index of the IL3-dependent proliferation.

As shown in Table 10, the compounds (I) and their lactones suppressed the increase of IL3-induced $^3$H-thymidine incorporation into FDC-P2 cells. It was thus suggested that the immunosuppressive compounds of this invention have the activity to suppress the IL3-dependent proliferation.

TABLE 10

| IL3 | Test substance | Dose (μg/ml) | $^3$H-thymidine uptake (cpm) | Suppression (%) |
|---|---|---|---|---|
| — | — | — | 1540 | — |
| + | — | — | 8315 | — |
| + | compound of Example 1 | 0.001 | 6858 | 21.5 |
| + | | 0.01 | 6572 | 25.7 |
| + | | 0.1 | 5203 | 45.9 |
| + | | 1 | 5029 | 48.5 |
| + | | 10 | 2750 | 82.1 |
| + | compound of Example 4 | 0.001 | 7754 | 8.3 |
| + | | 0.01 | 6557 | 25.9 |
| + | | 0.1 | 5861 | 36.2 |
| + | | 1 | 4922 | 50.1 |
| + | | 10 | 2902 | 79.9 |

(In the table, the marks '+' and '—' mean the presence of IL3 and the absence of IL3, respectively.)

Experimental Example 11 (Suppression of interleukin 6 (IL6) response of mouse spleen cells)

The spleen was resected from 8-week-old male BALB/c mice, and single cell suspension in the serum-free RPMI1640 culture medium was prepared, and thereafter cell pellets were obtained by centrifugation (1000 rpm, 5 minutes) of the suspension. Then a mixture of 9 parts of a 0.16 M ammonium chloride solution and 1 part of a 0.17 M Tris solution (pH 7.65) was added to lyse red blood cells, and the suspension was washed three times with the serum-free RPMI1640 culture medium. The obtained cells were suspended to the concentration of $5 \times 10^6$ cells/ml in the RPMI1640 culture medium supplemented with 20% FCS, $5 \times 10^{-5}$ M 2-mercaptoethanol, $2 \times 10^{-3}$ M L glutamine, $1 \times 10^{-3}$ sodium pyruvate and 25% of the supernatant of the culture of T24 human bladder carcinoma cell line as a source of interluekin 6. One hundred μl of this cell suspension and 100 μl of the test substance were mixed in each well of 96-well microculture plates, and cultured at 37° C. in an atmosphere of 5% carbon dioxide for 72 hours. After termination of the culture, 50 μl of the cell suspension was collected from each well. Three hundred μl of the RPMI1640 culture medium supplemented with 0.7% agarose gel, 20 μl of physiological saline containing 40% protein A-bound sheep red blood cells and 20 μl of 300-fold dilution of anti-mouse IgG anti-serum diluted in physiological saline were mixed in a test tube, and extended uniformly on Rohduck plates (Falcon Co. 1034). After gel formation by keeping still at room temperature for a few minutes, the plates were cultured at 37° C. in an atmosphere of 5% carbon dioxide for about 4 hours.

Three hundred μl of a 40-fold dilution of guinea pig complement in the serum-free RPMI1640 culture medium was added to each plate, which was then incubated for further 2 hours. The number of plaques formed was counted under stereoscopic microscope.

The results of this procedure are summarized in Table 11. SD in the Table means standard deviation. The percent suppression (%) was calculated by the following formula.

$$\text{percent suppression (\%)} = \left(1 - \frac{\text{No. of plaque with IL6 + test substance} - \text{No. of plaque without IL6}}{\text{No. of plaque with IL6 alone} - \text{No. of plaque without IL6}}\right) \times 100$$

TABLE 11

| Test substance | Dose (μg/ml) | Number of plaque (plaque/$1 \times 10^6$ cells ± SD) | Suppression (%) |
|---|---|---|---|
| — | — | 12 ± 2 | — |
| IL6 | — | 206 ± 12 | 0 |
| IL6 + compound of Example 1 | 2 | 60 ± 8 | 75.3 |
| | 0.2 | 78 ± 6 | 66.0 |
| | 0.02 | 108 ± 10 | 50.5 |
| | 0.002 | 130 ± 4 | 39.2 |

As shown in Table 11, it is evident that the compounds (I) and their lactones have the suppressive effect of the IL6 response does-dependent.

Experimental Example 12 (Suppression for mouse anti-sheep red blood cell antibody production)

Males 5- to 7-week-old BALB/c mice were immunized with sheep red blood cells (SRBC), and the spleen was resected three or four days later. By counting the plaque forming cells (PFC), suppressive effect on the production of the anti-sheep red blood cell antibody was examined as follows.

Experiment 1:

BALB/c mice were immunized with SRBC ($1 \times 10^7$ cells/mouse, intravenous administration), and ISP-I in the Example 1 was administered intraperitoneally for 4 consecutive days from the day of immunization. Four days after immunization (the next day of the final administration), the spleen was resected and the anti-sheep red blood cell antibody-producing cells were determined by the direct plaque method. At the same time the body weight of the mouse, wet weight of the thymus and the spleen, and numbers of spleen cells were also determined.

Experiment 2:

BALB/c mice were immunized with SRBC ($5 \times 10^7$ cells/mouse, intravenous administration), and the compound in the Example 5 was administered intraperitoneally for 4 consecutive days from the day of immunization. Four days after immunization (the next day of the final administration), the spleen was resected, and the anti-sheep red blood cell antibody-producing cells were determined by the direct plaque method. At the same time, the body weight of the mouse, wet weight of the thymus and the spleen, and numbers of spleen cells were also determined.

ministered intraperitoneally 6 times at the doses of 0.1 mg/kg/day from the next day of immunization. Eight days after immunization, the spleen was resected to prepare effector cells, with which the $^{51}$Cr release test was carried out as in Experimental Example 3, using EL4 cells as the target cells to measure the cytotoxic activity.

As shown in Table 13, it is evident that administration of the compound (I) or a lactone thereof suppresses the induction of allo-reactive cytotoxic T cells.

TABLE 13

| Test substance | | Amount of $^{51}$Cr release (cpm) | Cytotoxic activity (%) |
|---|---|---|---|
| Total radioactivity of target cells | — | 7235 | — |
| Target cells alone | — | 720 | — |
| Effector cells + target cells | | | |
| (100:1) | — | 2618 | 29 |
| (50:1) | — | 2340 | 25 |
| (25:1) | — | 1436 | 11 |
| Effector cells + target cells | | | |
| (100:1) | compound of Example 1 | 1543 | 13 |
| (50:1) | | 1258 | 8 |
| (25:1) | | 1046 | 5 |

Experimental Example 14 (Cytotoxicity to mouse L929 cells)

Cytotoxicity to mouse L929 cells was assayed as follows:

TABLE 12B

| Test substance | Dose (mg/kg/day) | Body weight (g) | Wet weight (mg) thymus | Wet weight (mg) spleen | Number of spleen cells ($\times 10^8$ cell) | Number of PFC $\times 10^3 / 1 \times 10^7$ cell | Number of PFC $\times 10^4$/spleen |
|---|---|---|---|---|---|---|---|
| — | — | 10 ± 1 | 47 ± 6 | 134 ± 6 | 0.9 ± 0.1 | 17.0 ± 8.5 | 15.4 ± 7.7 |
| Compound of Example 8 | 10 | 18 ± 1 | 25 ± 9 | 103 ± 30 | 1.3 ± 0.2 | 6.7 ± 1.2 | 8.5 ± 1.9 |

TABLE 12A

| Test substance | Dose (mg/kg/day) | Body weight (g) | Wet weight (mg) thymus | Wet weight (mg) spleen | Number of spleen cells ($\times 10^8$ cell) | Number of PFC $\times 10^3 / 1 \times 10^7$ cell | Number of PFC $\times 10^4$/spleen |
|---|---|---|---|---|---|---|---|
| Experiment 1 | | | | | | | |
| — | — | 25 ± 1 | 48 ± 12 | 237 ± 28 | 1.4 ± 0.2 | 2.2 ± 1.6 | 1.4 ± 0.8 |
| Compound of Example 1 | 0.3 | 23 ± 2 | 48 ± 5 | 202 ± 4 | 1.4 ± 0.3 | 1.4 ± 0.4 | 0.9 ± 0.3 |
| | 1 | 23 ± 1 | 50 ± 1 | 206 ± 32 | 1.3 ± 0.4 | 0.5 ± 0.2 | 0.3 ± 0.1 |
| | 3 | 19 ± 1 | 25 ± 14 | 137 ± 17 | 1.3 ± 0.2 | 0.2 ± 0.1 | 0.1 ± 0.0 |
| Experiment 2 | | | | | | | |
| — | — | 24 ± 1 | 58 ± 10 | 295 ± 18 | 2.4 ± 0.4 | 9.4 ± 3.9 | 21.6 ± 8.5 |
| Compound of Example 5 | 10 | 24 ± 1 | 52 ± 5 | 239 ± 40 | 2.3 ± 0.3 | 5.6 ± 1.7 | 12.9 ± 3.9 |

As shown in Table 12A and B, it is evident that the compound (I) and the lactones thereof have a suppressive effect on anti-sheep red blood cell antibody production, that is, they decrease PFC numbers per unit spleen cells numbers ($1 \times 10^7$ cells) and PFC number per total spleen cells numbers.

Experimental Example 13 (Suppression of allo-reactive cytotoxic T cells induced by immunization of mouse with allogenic cells)

Male BALB/c mice were immunized with spleen cells of C57BL/6 mice ($5 \times 10^7$ cells/mouse, intraperitoneal administration), and ISP-I in Example 1 was ad- L929 cells were suspended to the concentration of $1.5 \times 10^5$ cells/ml in the F12 culture medium supplemented with 10% FCS. One hundred µl of the suspension was added to each well of 96-well microculture plates, and cultured at 37° C. in an atmosphere of 5% carbon dioxide for 24 hours, to which 100 µl of the test solution was added and cultured for further 48 hours. After the culture, 100 µl of the supernatant was removed and the absorbancy at 550 nm was measured in the same way as the colormetry using MTT in Experimental Example 1. The percent suppression was calculated by the following formula used as the index of cytotoxicity.

$$\text{percent suppression (\%)} = 1 - \left(\frac{\text{absorbancy with test substance}}{\text{absorbancy without test substance}}\right) \times 100$$

The results are summarized in Table 14A and B.

TABLE 14A

| Test substance | Dose (μg/ml) | Absorbancy | Suppression (%) |
|---|---|---|---|
| — | — | 0.669 | — |
| Compound of Example 1 | 1 | 0.699 | 0 |
| | 10 | 0.693 | 0 |
| | 100 | 0.321 | 52.0 |

TABLE 14B

| Test substance | Dose (μg/ml) | Absorbancy | Suppression (%) |
|---|---|---|---|
| — | — | 0.573 | — |
| Compound of Example 5 | 0.1 | 0.775 | 0 |
| | 1 | 0.805 | 0 |
| | 10 | 0.749 | 0 |
| Compound of Example 6 | 0.1 | 0.732 | 0 |
| | 1 | 0.714 | 0 |
| | 10 | 0.733 | 0 |
| Compound of Example 7 | 0.1 | 0.799 | 0 |
| | 1 | 0.811 | 0 |
| | 10 | 0.696 | 0 |
| Compound of Example 8 | 1 | 0.817 | 0 |
| | 10 | 0.738 | 0 |
| | 100 | 0.023 | 96.0 |
| Compound of Example 9 | 1 | 0.749 | 0 |
| | 10 | 0.747 | 0 |
| | 100 | 0.567 | 1.0 |
| Compound of Example 10 | 1 | 0.722 | 0 |
| | 10 | 0.661 | 0 |
| | 100 | 0.023 | 96.0 |
| Compound of Example 11 | 1 | 0.710 | 0 |
| | 10 | 0.669 | 0 |
| | 100 | 0.047 | 91.8 |

As shown in Tables 14A and B, it is evident that the compounds (I) and their lactones show very low cytotoxicity to mouse L929 cells.

Experimental Example 15 (Cytotoxicity to various tumor cell lines)

Cytotoxicity to human tumor cell lines was examined as follows:

Cells of human cell lines, K562, MOLT4, U937, HL60, KATOIII, KB, PC-6, PC-14 and CCRF-CEM were separately suspended to the concentration of $2 \times 10^5$ cells/ml in the RPMI1640 culture medium supplemented with 20% FCS. Fifty μl of this suspension was added to each well of 96-well microculture plates to which 50 μl of the test solution had been added. After culturing at 37° C. in an atmosphere of 5% carbon dioxide for 72 hours, the absorbancy at 550 nm was measured in the same way as the colorimetry using MTT in Experimental Example 1, and the percent suppression was calculated in the same manner as in Experimental Example 14, which was used as the index of cytotoxicity. As shown in Tables 15A to 15F showing the results of the calculation, the cytotoxicity of the compounds (I) and their lactones to the various cultured human tumor cell lines is weak, with the concentration of 50% inhibition ($IC_{50}$) being 10 μg/ml or more.

TABLE 15A

| | Compound of Example 1 | | |
|---|---|---|---|
| Cell lines | Dose (μg/ml) | Absorbancy | Suppression (%) |
| K562 | 0 | 0.990 | — |
| | 0.1 | 0.886 | 10.6 |
| | 1.0 | 0.905 | 8.6 |
| | 10.0 | 0.929 | 6.2 |
| | 100.0 | 0.583 | 41.1 |
| MOLT4 | 0 | 0.618 | — |
| | 0.1 | 0.560 | 9.4 |
| | 1.0 | 0.559 | 9.5 |
| | 10.0 | 0.499 | 19.3 |
| | 100.0 | 0.074 | 88.0 |
| U937 | 0 | 0.642 | — |
| | 0.1 | 0.619 | 3.6 |
| | 1.0 | 0.567 | 11.7 |
| | 10.0 | 0.497 | 22.6 |
| | 100.0 | 0.156 | 75.7 |
| HL60 | 0 | 0.631 | — |
| | 0.1 | 0.402 | 36.3 |
| | 1.0 | 0.390 | 38.2 |
| | 10.0 | 0.377 | 40.3 |
| | 100.0 | 0.101 | 84.0 |
| KATOIII | 0 | 0.961 | — |
| | 0.01 | 0.990 | 0 |
| | 0.1 | 0.972 | 0 |
| | 1.0 | 0.961 | 0 |
| | 10.0 | 0.869 | 9.6 |
| | 100.0 | 0.041 | 95.7 |

TABLE 15B

| | Compound of Example 1 | | |
|---|---|---|---|
| Cell lines | Dose (μg/ml) | Absorbancy | Suppression (%) |
| KB | 0 | 0.888 | — |
| | 0.01 | 0.898 | 0 |
| | 0.1 | 0.865 | 2.6 |
| | 1.0 | 0.879 | 1.0 |
| | 10.0 | 0.886 | 0.2 |
| | 100.0 | 0.025 | 97.2 |
| PC-6 | 0 | 0.272 | — |
| | 0.01 | 0.244 | 10.3 |
| | 0.1 | 0.245 | 9.9 |
| | 1.0 | 0.209 | 23.2 |
| | 10.0 | 0.202 | 25.7 |
| | 100.0 | 0.000 | 100.0 |
| PC-14 | 0 | 0.787 | — |
| | 0.01 | 0.801 | 0 |
| | 0.1 | 0.770 | 2.2 |
| | 1.0 | 0.732 | 7.0 |
| | 10.0 | 0.751 | 4.6 |
| | 100.0 | 0.074 | 90.6 |
| CCRF-CEM | 0 | 0.708 | — |
| | 0.01 | 0.678 | 4.2 |
| | 0.1 | 0.709 | 0 |
| | 1.0 | 0.660 | 6.8 |
| | 10.0 | 0.637 | 10.0 |
| | 100.0 | 0.013 | 98.2 |

TABLE 15C

| | Compound of Example 4 | | |
|---|---|---|---|
| Cell lines | Dose (μg/ml) | Absorbancy | Suppression (%) |
| K562 | 0 | 0.614 | — |
| | 0.1 | 0.524 | 14.7 |
| | 1.0 | 0.563 | 8.3 |
| | 10.0 | 0.525 | 14.5 |
| | 100.0 | 0.007 | 98.9 |
| MOLT4 | 0 | 0.408 | — |
| | 0.1 | 0.351 | 14.0 |
| | 1.0 | 0.350 | 14.2 |
| | 10.0 | 0.315 | 22.8 |
| | 100.0 | 0.012 | 97.1 |
| U937 | 0 | 0.373 | — |
| | 0.1 | 0.313 | 16.1 |
| | 1.0 | 0.384 | 0 |

TABLE 15C-continued

| | Compound of Example 4 | | |
|---|---|---|---|
| Cell lines | Dose (μg/ml) | Absorbancy | Suppression (%) |
| | 10.0 | 0.362 | 2.9 |
| | 100.0 | 0.004 | 99.0 |
| HL60 | 0 | 0.346 | — |
| | 0.1 | 0.265 | 23.4 |
| | 1.0 | 0.300 | 13.3 |
| | 10.0 | 0.273 | 21.1 |
| | 100.0 | 0.008 | 97.7 |
| KATOIII | 0 | 0.430 | — |
| | 0.1 | 0.407 | 5.3 |
| | 1.0 | 0.401 | 6.7 |
| | 10.0 | 0.319 | 25.8 |
| | 100.0 | 0.009 | 97.9 |

TABLE 15D

| | Compound of Example 4 | | |
|---|---|---|---|
| Cell lines | Dose (μg/ml) | Absorbancy | Suppression (%) |
| KB | 0 | 1.092 | — |
| | 0.1 | 0.884 | 19.0 |
| | 1.0 | 1.065 | 2.5 |
| | 10.0 | 0.726 | 33.5 |
| | 100.0 | 0.012 | 99.0 |
| PC-6 | 0 | 0.291 | — |
| | 0.1 | 0.247 | 15.1 |
| | 1.0 | 0.273 | 6.2 |
| | 10.0 | 0.271 | 6.9 |
| | 100.0 | 0.014 | 95.2 |
| PC-14 | 0 | 0.633 | — |
| | 0.1 | 0.656 | 0 |
| | 1.0 | 0.679 | 0 |
| | 10.0 | 0.657 | 0 |
| | 100.0 | 0.030 | 95.3 |
| CCRF-CEM | 0 | 0.636 | — |
| | 0.1 | 0.564 | 11.3 |
| | 1.0 | 0.556 | 12.6 |
| | 10.0 | 0.389 | 37.4 |
| | 100.0 | 0.004 | 99.4 |

TABLE 15E

| Cell lines | Test substance | Dose (μg/ml) | Absorbancy | Suppression (%) |
|---|---|---|---|---|
| K562 | — | — | 0.836 | — |
| | Compound of Example 5 | 0.1 | 0.823 | 1.6 |
| | | 1.0 | 0.810 | 3.1 |
| | | 10.0 | 0.780 | 6.7 |
| | Compound of Example 6 | 0.1 | 0.823 | 1.6 |
| | | 1.0 | 0.798 | 4.5 |
| | | 10.0 | 0.811 | 3.0 |
| MOLT4 | — | — | 0.620 | — |
| | Compound of Example 5 | 0.1 | 0.591 | 4.7 |
| | | 1.0 | 0.588 | 5.2 |
| | | 10.0 | 0.508 | 18.1 |
| | Compound of Example 6 | 0.1 | 0.615 | 0.8 |
| | | 1.0 | 0.599 | 3.4 |
| | | 10.0 | 0.567 | 8.5 |
| U937 | — | — | 0.484 | — |
| | Compound of Example 5 | 0.1 | 0.462 | 4.5 |
| | | 1.0 | 0.485 | 0 |
| | | 10.0 | 0.416 | 0 |
| | Compound of Example 6 | 0.1 | 0.439 | 14.0 |
| | | 1.0 | 0.436 | 9.9 |
| | | 10.0 | 0.435 | 10.1 |
| HL60 | — | — | 0.746 | — |
| | Compound of Example 5 | 0.1 | 0.593 | 20.5 |
| | | 1.0 | 0.657 | 11.9 |
| | | 10.0 | 0.590 | 20.9 |
| | Compound of Example 6 | 0.1 | 0.619 | 16.0 |
| | | 1.0 | 0.589 | 21.0 |
| | | 10.0 | 0.627 | 17.0 |
| CCRF-CEM | — | — | 0.503 | — |
| | Compound of Example 5 | 0.1 | 0.485 | 3.6 |
| | | 1.0 | 0.466 | 7.4 |
| | | 10.0 | 0.394 | 21.7 |

TABLE 15E-continued

| Cell lines | Test substance | Dose (μg/ml) | Absorbancy | Suppression (%) |
|---|---|---|---|---|
| | Compound of Example 6 | 0.1 | 0.463 | 8.0 |
| | | 1.0 | 0.457 | 9.1 |
| | | 10.0 | 0.475 | 5.6 |
| KB | — | — | 0.730 | — |
| | Compound of Example 5 | 0.1 | 0.761 | 0 |
| | | 1.0 | 0.734 | 0 |
| | | 10.0 | 0.711 | 2.6 |
| | Compound of Example 6 | 0.1 | 0.771 | 0 |
| | | 1.0 | 0.728 | 0.3 |
| | | 10.0 | 0.707 | 3.2 |
| PC-14 | — | — | 0.474 | — |
| | Compound of Example 5 | 0.1 | 0.420 | 11.4 |
| | | 1.0 | 0.396 | 16.5 |
| | | 10.0 | 0.352 | 25.7 |
| | Compound of Example 6 | 0.1 | 0.372 | 21.5 |
| | | 1.0 | 0.405 | 14.6 |
| | | 10.0 | 0.351 | 25.9 |

TABLE 15F

| Cell lines | Test substance | Dose (μg/ml) | Absorbancy | Suppression (%) |
|---|---|---|---|---|
| K562 | — | — | 0.385 | — |
| | Compound of Example 7 | 0.1 | 0.387 | 0 |
| | | 1.0 | 0.332 | 13.8 |
| | | 10.0 | 0.302 | 21.6 |
| | Compound of Example 8 | 0.1 | 0.327 | 15.1 |
| | | 1.0 | 0.321 | 16.6 |
| | | 10.0 | 0.298 | 22.6 |
| | Compound of Example 9 | 0.1 | 0.378 | 1.8 |
| | | 1.0 | 0.364 | 5.5 |
| | | 10.0 | 0.317 | 17.7 |
| | Compound of Example 10 | 0.1 | 0.390 | 0 |
| | | 1.0 | 0.343 | 10.9 |
| | | 10.0 | 0.311 | 19.2 |
| | Compound of Example 11 | 0.1 | 0.317 | 17.7 |
| | | 1.0 | 0.337 | 12.5 |
| | | 10.0 | 0.257 | 34.5 |
| MOLT4 | — | — | 0.145 | — |
| | Compound of Example 7 | 0.1 | 0.107 | 26.2 |
| | | 1.0 | 0.123 | 15.2 |
| | | 10.0 | 0.100 | 31.0 |
| | Compound of Example 8 | 0.1 | 0.142 | 2.1 |
| | | 1.0 | 0.137 | 5.5 |
| | | 10.0 | 0.133 | 8.3 |
| | Compound of Example 9 | 0.1 | 0.111 | 23.4 |
| | | 1.0 | 0.132 | 9.0 |
| | | 10.0 | 0.142 | 2.1 |
| | Compound of Example 10 | 0.1 | 0.148 | 0 |
| | | 1.0 | 0.159 | 0 |
| | | 10.0 | 0.170 | 0 |
| | Compound of Example 11 | 0.1 | 0.182 | 0 |
| | | 1.0 | 0.150 | 0 |
| | | 10.0 | 0.128 | 11.7 |
| U937 | — | — | 0.583 | — |
| | Compound of Example 7 | 0.1 | 0.588 | 0 |
| | | 1.0 | 0.593 | 0 |
| | | 10.0 | 0.551 | 5.5 |
| | Compound of Example 8 | 0.1 | 0.590 | 0 |
| | | 1.0 | 0.580 | 0.5 |
| | | 10.0 | 0.513 | 12.0 |
| | Compound of Example 9 | 0.1 | 0.640 | 0 |
| | | 1.0 | 0.592 | 0 |
| | | 10.0 | 0.584 | 0 |
| | Compound of Example 10 | 0.1 | 0.545 | 6.5 |
| | | 1.0 | 0.541 | 7.2 |
| | | 10.0 | 0.517 | 11.3 |
| | Compound of Example 11 | 0.1 | 0.598 | 0 |
| | | 1.0 | 0.583 | 0 |
| | | 10.0 | 0.449 | 23.0 |
| HL60 | — | — | 0.522 | — |
| | Compound of Example 7 | 0.1 | 0.432 | 17.2 |
| | | 1.0 | 0.427 | 18.2 |
| | | 10.0 | 0.428 | 18.0 |
| | Compound of Example 8 | 0.1 | 0.434 | 16.9 |
| | | 1.0 | 0.445 | 14.8 |
| | | 10.0 | 0.418 | 19.9 |
| | Compound of | 0.1 | 0.450 | 13.8 |

TABLE 15F-continued

| Cell lines | Test substance | Dose (µg/ml) | Absorbancy | Suppression (%) |
|---|---|---|---|---|
| | Example 9 | 1.0 | 0.435 | 16.7 |
| | | 10.0 | 0.413 | 20.9 |
| | Compound of Example 10 | 0.1 | 0.447 | 14.4 |
| | | 1.0 | 0.415 | 20.5 |
| | | 10.0 | 0.406 | 22.3 |
| | Compound of Example 11 | 0.1 | 0.475 | 9.0 |
| | | 1.0 | 0.456 | 12.6 |
| | | 10.0 | 0.381 | 27.0 |
| KB | — | | 0.730 | — |
| | Compound of Example 7 | 0.1 | 0.726 | 0.5 |
| | | 1.0 | 0.695 | 4.8 |
| | | 10.0 | 0.493 | 32.5 |
| | Compound of Example 8 | 0.1 | 0.741 | 0 |
| | | 1.0 | 0.749 | 0 |
| | | 10.0 | 0.706 | 3.3 |
| | Compound of Example 9 | 0.1 | 0.778 | 0 |
| | | 1.0 | 0.762 | 0 |
| | | 10.0 | 0.696 | 4.7 |
| | Compound of Example 10 | 0.1 | 0.743 | 0 |
| | | 1.0 | 0.735 | 0 |
| | | 10.0 | 0.610 | 16.4 |
| | Compound of Example 11 | 0.1 | 0.679 | 7.0 |
| | | 1.0 | 0.688 | 5.8 |
| | | 10.0 | 0.510 | 30.1 |
| PC-14 | — | | 0.474 | — |
| | Compound of Example 7 | 0.1 | 0.446 | 5.9 |
| | | 1.0 | 0.424 | 10.5 |
| | | 10.0 | 0.315 | 33.5 |
| | Compound of Example 8 | 0.1 | 0.452 | 4.6 |
| | | 1.0 | 0.425 | 10.3 |
| | | 10.0 | 0.326 | 31.2 |
| | Compound of Example 9 | 0.1 | 0.404 | 14.8 |
| | | 1.0 | 0.441 | 7.0 |
| | | 10.0 | 0.374 | 21.1 |
| | Compound of Example 10 | 0.1 | 0.433 | 8.6 |
| | | 1.0 | 0.411 | 13.3 |
| | | 10.0 | 0.317 | 33.1 |
| | Compound of Example 11 | 0.1 | 0.443 | 6.5 |
| | | 1.0 | 0.413 | 12.7 |
| | | 10.0 | 0.284 | 40.0 |
| CCRF-CEM | — | | | |
| | Compound of Example 7 | 0.1 | 0.681 | 1.6 |
| | | 1.0 | 0.653 | 5.6 |
| | | 10.0 | 0.587 | 15.2 |
| | Compound of Example 8 | 0.1 | 0.720 | 0 |
| | | 1.0 | 0.694 | 0 |
| | | 10.0 | 0.665 | 3.9 |
| | Compound of Example 9 | 0.1 | 0.702 | 0 |
| | | 1.0 | 0.696 | 0 |
| | | 10.0 | 0.680 | 1.7 |
| | Compound of Example 10 | 0.1 | 0.672 | 2.9 |
| | | 1.0 | 0.647 | 6.5 |
| | | 10.0 | 0.645 | 6.8 |
| | Compound of Example 11 | 0.1 | 0.694 | 0 |
| | | 1.0 | 0.663 | 4.2 |
| | | 10.0 | 0.603 | 12.9 |

Formulation Example

| (1) Soft capsules (in one capsule) | |
|---|---|
| compound of Example 1 | 30 mg |
| polyethyleneglycol-300 | 300 mg |
| polysorbate 80 | 20 mg |
| total | 350 mg |

Procedure of preparation

Polyethyleneglycol-300 and polysorbate 80 are added to the compound of Example 1, and the mixture is filled in soft capsules.

| (2) Injections (in one ampoule, 10 ml) | |
|---|---|
| compound of Example 1 | 0.3% |
| polyethyleneglycol-300 | 20% |
| ethanol | 60% |

A sufficient quantity of distilled water is added to make the total amount 10 ml.

Procedure of preparation

Ethanol and polyethyleneglycol-300 are added to the compound of Example 1 for dissolution and a sufficient quantity of distilled water is added thereto to make the whole volume.

Thus, an injection containing 30 ml of the compound of Example 1 in 10 ml in an ampoule is obtained.

We claim:

1. A method for suppression of rejection in transplantation of organs or bone marrow which comprises administering at least one compound selected form compounds of formula

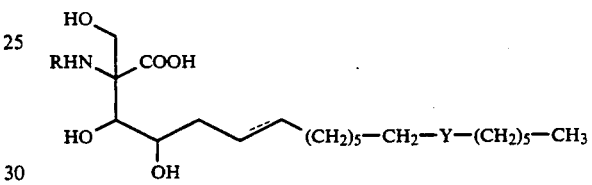

wherein R represents a hydrogen atom or an alkanoyl having 2 to 5 carbon atoms, benzoyl or phenacetyl, Y represents carbonyl or hydroxymethylene and ⁓ represents a single bond or a double bond and their lactones in an effective amount.

2. A method as claimed in claim 1 which comprises administering at least one compound selected form the compounds of formula

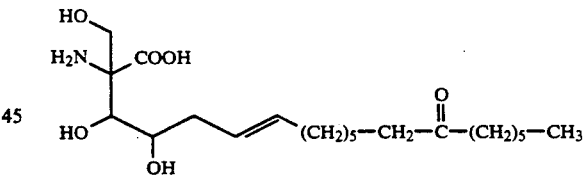

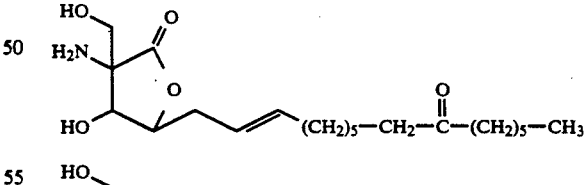

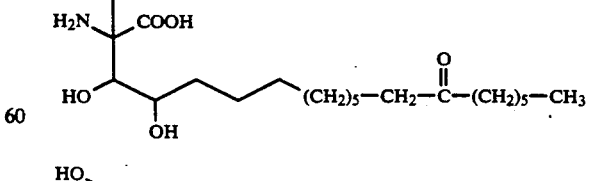

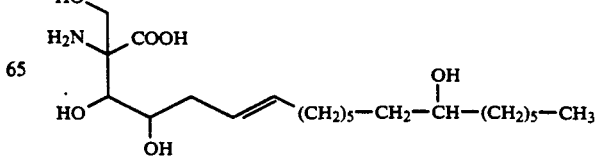

-continued
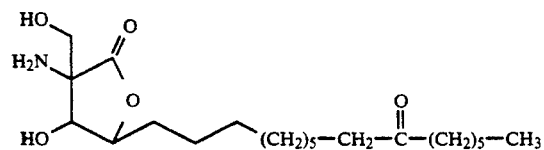
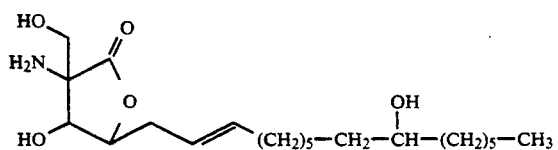
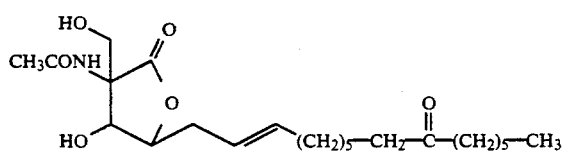
-continued
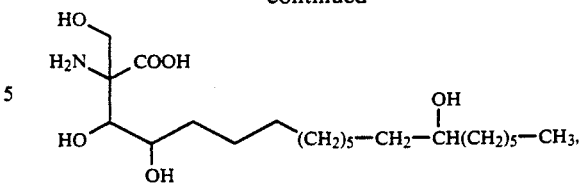
and
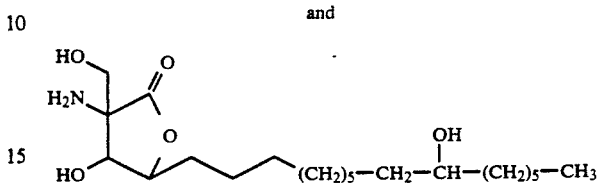
in an effective amount.
3. A compound of formula
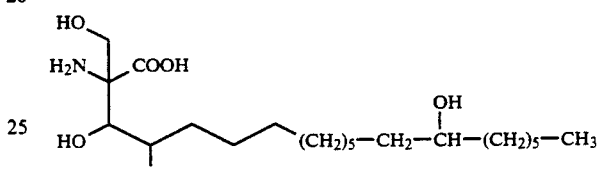
or its lactone.
* * * * *